United States Patent [19]

Umeno et al.

[11] Patent Number: 4,613,373
[45] Date of Patent: Sep. 23, 1986

[54] TETRAARYLBORON-AMMONIUM COMPLEXES AND THEIR USES

[75] Inventors: Masayuki Umeno, Chigasaki; Akitomo Wakabayashi, Atsugi; Kazuo Tomozane, Isehara; Sumio Wakabayashi, Atsugi; Hitoshi Okamoto, Tamano; Junji Yokoi, Ikoma, all of Japan

[73] Assignees: Hokko Chemical Industry Co., Ltd.; Mitsui Engineering & Shipbuilding Co., Ltd.; Nippon Paint Co., Ltd., all of Tokyo, Japan

[21] Appl. No.: 694,064

[22] Filed: Jan. 23, 1985

[30] Foreign Application Priority Data

Jan. 24, 1984 [JP]  Japan .................................. 59-9516
May 24, 1984 [JP]  Japan ................................ 59-103644

[51] Int. Cl.⁴ ..................... C09D 5/14; C09D 5/16; C07F 5/02; A01N 99/14
[52] U.S. Cl. ..................... 106/18.3; 514/64; 546/13; 548/110
[58] Field of Search ........................ 546/13; 548/110; 514/64; 106/18.3

[56] References Cited

U.S. PATENT DOCUMENTS 3,211,679  10/1965  Opdegraff ............................ 546/13

*Primary Examiner*—Robert T. Bond
*Attorney, Agent, or Firm*—Larson and Taylor

[57] ABSTRACT

New tetraarylboron-ammonium complexes having the general formula:

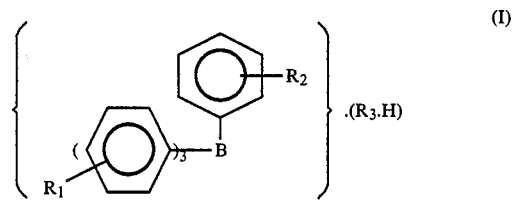

wherein $R_1$ represents a hydrogen or a halogen atom or a lower alkyl group; $R_2$ represents a halogen atom or a lower alkyl or a lower alkenyl group; and $R_3$ represents a heterocyclic amine are provided as active ingredient of anti-fouling paint and also of antiseptic, antifungal agent. These compounds exhibit remarkably long-lasting anti-fouling activities against substantially all kinds of aquatic organisms including slimes with acceptably low toxicity against human beings and also exhibit high antimicrobial activities against various fungi, bacteria and yeasts.

5 Claims, No Drawings

TETRAARYLBORON-AMMONIUM COMPLEXES AND THEIR USES

FIELD OF THE INVENTION

This invention relates to tetraarylboron-ammonium complexes as new compounds and their uses as antifouling paint, antiseptic and antifungal agents and the like.

BACKGROUND OF THE INVENTION

It has already been proposed that certain arylboron compounds are used as antifouling agent. Thus, Japanese Patent Publication No. 1571/79 discloses tetraphenylboron compounds having the general formula:

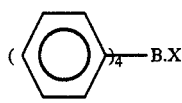

wherein X represents a potassium atom, an ammonium radical or a quaternary organic nitrogen-containing group which may form a nitrogen-containing heterocyclic group and has been exemplified by pyridinium, 4-methylpyridinium and 3-bromopyridinium group. U.S. Pat. No. 3,211,679 proposes triphenylboron compounds having the general formula:

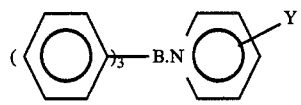

wherein Y represents a hydrogen atom, a halogen atom or a lower alkyl group, as antifouling agent.

As is well-known and experienced, the attachment and growth of a variety of aquatic organisms including small animals such as barnacles, serpulae, *Hydroides norvegica* (Gunnerus), sea squirts, sea mussels, oysters, etc.; algae such as sea lettuces, green lavers, eclocarpus, ulotrichales, etc.; and various bacteria, molds and diatoms generally called "slimes" onto ship's hull, particularly bottom and water line thereof, internal surfaces of intake and cooling pipes in power stations and various structures in sea and fresh water such as fish preserves, fishing nets and others result in a number of serious drawbacks from the maintenance and conservation points of view. Thus, in cases of ships, frictional resistance of the hull to passage through water is substantially increased, resulting in large economical losses such as decrease in fuel efficiency and maximum speed of the vessel and in necessity of periodic costly operations for the removal of such accumulated foulings. In cases of fish preserves and fishing nets, there occur such serious damages as tardy growth of bred fishes and oxygen-deficiency, whereas in case of a fixed shore net, such deficiencies as floating off of the net and resulting poor catch of fishes. For internal surfaces of cooling pipes and the like, there are such faults as clogging of heat exchangers and resulting interruption of the operation and poor cooling efficiency.

Hitherto, various measures have been proposed to prevent the attachment and growth of aquatic organisms on ship's hull and other aquatic structures in sea and fresh water. Most typically, there have been used many kinds of antifouling paints of which active ingredients are cuprous oxide, copper rhodanide, organotin compounds, organotin polymers, thiocarbamates and others. Certain tetraphenylboron compounds have also been proposed in Japanese Patent Publication No. 1571/79 above-referred to as low-toxicity antifouling agents, but they are still not perfectly satisfactory in their durability of the antifouling activities.

We have made many investigations, with the intention of obtaining new organoboron compounds having an effective antifouling activity over a prolonged period of time with retention of such low toxicity as shown in the known tetraphenylboron compounds above-mentioned, on the preparation of a number of organoboron compounds and on tests for evaluating the utilities of these compounds as antifouling agent. As a result, we have found that a series of new tetraarylboron-ammonium complexes as hereinafter defined exhibit unexpectedly long-lasting antifouling activities with satisfactorily low toxicity, thus making them appraisable to be such superior as antifouling agent to the known tetraphenylboron compounds.

We have extended our studies on these new complex compounds to their other properties and found that they also possess high anti-microbial activities against, for example, fungi such as genera Aspergillus, Penicillium, Rhizopus and Fusarium; bacteria such as genera Bacillus and Pseudomonas; and yeasts and are thus useful as antibacterial and antifungal agents for non-medicinal uses, particularly as antiseptic and antifungal agents for industrial uses.

SUMMARY OF THE INVENTION

According to the first aspect of this invention, therefore, there is provided as a new compound a tetraarylboron-ammonium complex having general formula (I):

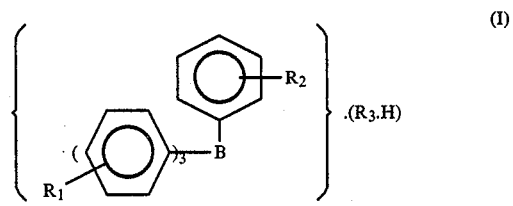

wherein $R_1$ represents a hydrogen atom, a halogen atom or a lower alkyl group; $R_2$ represents a halogen atom, a lower alkyl group or a lower alkenyl group; and $R_3$ represents a heterocyclic amine.

The tetraarylboron-ammonium complexes of general formula (I) according to this invention are chemically stable and exhibit an excellent antifouling effect and also high antibacterial and antifungal activities over wide pH ranges of both the acidic and alkaline natures. They do not tend to precipitate and/or discolor even in the coexistence of various metal salts and can be incorporated into various plastic compositions. Therefore, the tetraarylboron-ammonium complexes of general formula (I) may be used advantageously not only as antifouling agent but also as antibacterial, disinfectant, antiseptic and antifungal agents in many industrial applications.

According to the second aspect of this invention, therefore, there is provided an antifouling paint comprising as the antifouling active ingredient a tetraarylboron-ammonium complex having general formula (I) above-defined.

According to the third aspect of this invention, there is provided an antiseptic, antigungal agent comprising as active ingredient a tetraarylboron-ammonium complex having general formula (I) above-defined.

DETAILED DESCRIPTION OF THE INVENTION

Tetraarylboron-ammonium complexes of general formula (I)

In the tetraarylboron-ammonium complexes of general formula (I) according to this invention, $R_1$ and $R_2$ each are preferably bromine, chlorine or fluorine atom when they represent a halogen atom; methyl, ethyl, propyl, isopropyl, butyl or isobutyl group when they represent a lower alkyl group. When $R_2$ represents a lower alkenyl group, it is preferably vinyl group. The term "lower" means a group containing 1 to 6 carbon atoms when used in respect of alkyl and a group containing 2 to 6 carbon atoms when used in respect of alkenyl. The term "a heterocyclic amine" used with respect to $R_3$ means a five- or six-membered nitrogen-containing heterocyclic ring and preferably pyridine, imidazole or methylimidazole ring. ($R_3$.H) represents a quaternary ammonium group, preferably pyridinium, imidazolium or methylimidazolium group.

Typical examples of the tetraarylboron-ammonium complexes according to this invention are shown in Table 1 below. The compound numbers given in Table 1 are also referred to in Examples hereinafter given.

TABLE 1

| Compound No. | $R_1$-⌬ | $R_2$-⌬ | $R_3$ | Melting point (°C.) | Elemental Analysis Found C (%) | H (%) | Calculated C (%) | H (%) |
|---|---|---|---|---|---|---|---|---|
| 1 | $CH_3$-⌬- | $CH_3$-⌬- | ⌬N— (pyridine) | 183–185 | 86.8 | 7.4 | 87.0 | 7.5 |
| 2 | " | " | methylimidazole | 163–165 | 84.0 | 7.5 | 83.9 | 7.6 |
| 3 | ⌬-CH$_3$ (meta) | ⌬-CH$_3$ (meta) | pyridine | 136–138 | 87.1 | 7.4 | 87.1 | 7.5 |
| 4 | " | " | methylimidazole | 169–172 | 83.8 | 7.6 | 83.9 | 7.6 |
| 5 | Cl-⌬- | Cl-⌬- | pyridine | 157–161 | 64.7 | 4.1 | 64.9 | 4.1 |
| 6 | " | " | methylimidazole | 156–160 | 62.1 | 4.2 | 62.2 | 4.3 |
| 7 | F-⌬- | F-⌬- | pyridine | 194–198 | 73.8 | 4.7 | 73.9 | 4.7 |

TABLE 1-continued

| Compound No. | R₁ ⌬ | R₂ ⌬ | R₃ | Melting point (°C.) | Found C (%) | Found H (%) | Calculated C (%) | Calculated H (%) |
|---|---|---|---|---|---|---|---|---|
| 8 | " | " | ⌬N-N(H)-CH₃ (2-methylimidazole) | 205–207 | 70.5 | 5.0 | 70.9 | 4.9 |
| 9 | phenyl | CH₂=CH–phenyl | pyridine (N—) | 195–197 | 87.5 | 6.4 | 87.6 | 6.6 |
| 10 | " | " | ⌬N-N(H)-CH₃ (2-methylimidazole) | 234–236 | 84.1 | 6.9 | 84.2 | 6.8 |
| 11 | " | i-C₃H₇–phenyl | pyridine (N—) | 190–193 | 87.0 | 7.3 | 87.1 | 7.3 |

Thus, particular examples of the new compounds of general formula (I) according to this invention includes the following:

tetra(4-methylphenyl)boron-pyridinium complex;
tetra(4-methylphenyl)boron-2-methylimidazolium complex;
tetra(3-methylphenyl)boron-pyridinium complex;
tetra(3-methylphenyl)boron-2-methylimidazolium complex;
tetra(4-chlorophenyl)boron-pyridinium complex;
tetra(4-chlorophenyl)boron-2-methylimidazolium complex;
tetra(4-fluorophenyl)boron-pyridinium complex;
tetra(4-fluorophenyl)boron-2-methylimidazolium complex;
triphenyl-(4-vinyl)phenyl-boron-pyridinium complex;
triphenyl-(4-vinyl)phenyl-boron-2-methylimidazolium complex; and
triphenyl-(4-isopropyl)phenyl-boron-pyridinium complex.

According to a preferred embodiment of the first aspect of this invention, there is provided a tetraarylboron-ammonium complex of general formula (Ia):

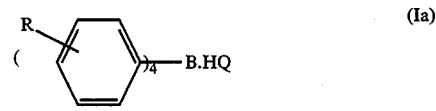

wherein R represents a (C₁-C₄) alkyl group, particularly methyl and ethyl, or a chlorine or fluorine atom and Q represents a pyridine, imidazole or methylimidazole group.

The tetraarylboron-ammonium complexes of general formula (I) according to this invention may be prepared by reacting a tetraarylboron sodium of general formula (II) with a heterocyclic amine.hydrohalogenide of general formula (III) according to the following reaction formula:

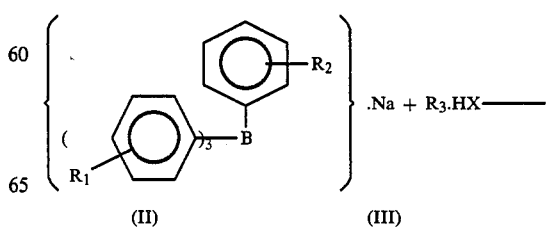

-continued

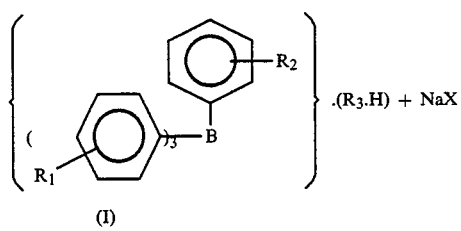

wherein X represents a halogen atom and $R_1$, $R_2$ and $R_3$ have the same meanings as defined above.

Some details of the preparation of the compounds of general formula (I) are given below.

The starting compound, a tetraarylboron sodium of general formula (II), may be prepared by the following procedures:

(i) Preparation of a compound of general formula (II) wherein $R_1 = R_2$

Into a solution of 4 moles or higher moles of either an arylmagnesium halide of the formula

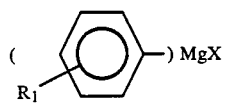

where $R_1$ and X have the same meanings as defined above or an aryllithium of the formula

where $R_1$ has the same meaning as defined above in diethylether or tetrahydrofuran is added dropwise 1 mole of boron trifluoride ethyl etherate as such or in the form of a solution in a solvent such as toluene under cooling with stirring, and the resulting mixture is refluxed for 1 hour. After cooling, a sodium source such as aqueous solution of an excess amount of sodium chloride, sodium carbonate or sodium hydroxide is added dropwise to the reaction solution. After the completion of the reaction, the organic phase separated as the upper layer is taken up, from which the solvent is distilled off, leaving colorless crystals. The crystals are washed with a non-polar organic solvent such as toluene and dried to afford the desired tetraarylboron sodium of general formula (II) as colorless crystals. If necessary, the crystals are purified by recrystallization from a lower alkanol such as ethanol and isopropanol.

(ii) Preparation of a compound of general formula (II) wherein $R_1 \neq R_2$

The reaction between an arylmagnesium halide or an aryllithium and boron trifluoride ethyl etherate is carried out in the same mannwer as in (i) above and from the resulting reaction solution is isolated symmetric triarylboron of the formula

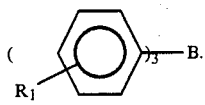

Alternatively, the reaction between an arylmagnesium halide or an aryllithium and boron trifluoride ethyl etherate is conducted under such controlled condition that the molar ratio of the reactants is strictly 3:1 from the start of the reaction to produce symmetric triarylboron. In either cases, then, the introduction of another aryl group of the formula

where $R_2$ is a substituent different from the substituent $R_1$ on each aryl group of the resulting triarylboron is effected to give asymmetric tetraarylboron.

The preparation of a compound of general formula (I) by the reaction between a compound of general formula (II) and a compound of general formula (III) may be carried out as follows:

A tetraarylboron sodium of general formula (II) prepared as above and a heterocyclic amine hydrohalogenide of general formula (III) are dissolved together in an inert polar solvent, for example a lower alkanol such as methanol, ethanol and isopropanol or a ketone such as acetone. The resulting mixture is stirred at 10°-60° C. for about 30 minutes to 2 hours to complete the desired reaction. The reaction solvent as above-exemplified may be used singly or in the form of a mixture. Usually, the reaction product may be recovered from the reaction mixture by distilling off the solvent therefrom whereby depositing crystals in the concentrated mixture, separating the crystals by filtration, washing the crystals to remove inorganic salts adhered thereto and drying the crystals, the desired complex of general formula (I) in high purity. In cases where the reaction product is in the form of crystals deposited in the solvent at the completion of the reaction, the crystals may be filtered directly.

The desired product, tetraarylboron-ammonium complex of general formula (I), may be further purified, if necessary, by recrystallization from a solvent such as methanol, ethanol, chloroform and dimethylformamide.

The following Examples 1 to 7 illustrate the preparation of compounds, Example 1 being for the preparation of a compound of general formula (II) and Examples 2-7 being for the preparation of compounds of general formula (I).

EXAMPLE 1

This Example illustrates the production of tetra(4-chloro-phenyl)boron sodium which is the starting material used in the production of the complex according to this invention.

4-Chlorophenylmagnesium chloride (1.2 moles) which had been obtained from para-dichlorobenzene and magnesium was dissolved in tetrahydrofuran, and 800 ml of the resultant solution were introduced into a four-necked flask of 2 l capacity to which was then added dropwise a solution (50 ml) of boron trifluoride di-ethyletherate (35.5 g, 0.25 moles) in toluene at 20° to 30° C. under cooling of the reaction system in a water bath and with stirring. The resultant mixture was heated under reflux for one hour. When the reaction was complete, the reaction solution was cooled to ambient temperature and to this solution was added dropwise 200 ml of a saturated aqueous sodium carbonate solution. On standing, the solution separated into the upper organic phase and lower aqueous phase. The organic phase separated was distilled to remove the solvent, affording colorless crystals. The resulting crystals were triturated with 300 ml of toluene, filtered off, washed twice with 100 ml portions of toluene and dried to give 106 g (yield: 88%) of the titled compound as colorless crystal. Melting point 310° C.

EXAMPLE 2

This Example illustrates the production of tetra(4-chlorophenyl)boron-pyridinium complex (Compound No. 5 in Table 1) according to this invention.

A 500 ml flask was charged with a solution of 24.0 g (0.05 moles) of tetra(4-chlorophenyl)boron sodium in 200 ml of methanol, to which was added dropwise a solution of 5.3 g (0.05 moles) of pyridine hydrochloride in 50 ml of methanol with stirring. When the addition was complete, the resultant mixture was stirred for one hour to complete the reaction. Subsequently, the solvent was distilled out of the reaction solution, and the crystals thus deposited were triturated with 100 ml of water, filtered off, washed with water and dried to afford 24.9 g (yield 92.6%) of the titled compound as colorless crystal. Melting point 157° to 161° C.

Elemental analysis: Found: C, 64.7%; H, 4.1%. Calcd.: C, 64.9%, H, 4.1%.

EXAMPLE 3

Production of tetra(4-chlorophenyl)boron-pyridinium complex (Compound No. 5)

The procedure of Example 2 was repeated except that pyridine hydrochloride is substituted by pyridine hydrobromide. There was afforded 26.0 g (yield: 96.8%) of the titled compound as colorless crystal. Melting point 157° to 161° C.

Elemental analysis: Found: C, 64.6%; H, 4.2%. Calcd.: C, 64.9%; H, 4.1%.

EXAMPLE 4

Production of tetra(4-fluorophenyl)boron-2-methylimidazolium complex (Compound No. 8)

An 100 ml flask was charged with a solution of 4.1 g (0.01 mole) of tetra(4-fluorophenyl)boron sodium in 40 ml of ethanol, to which was added dropwise a solution of 1.2 g (0.01 moles) of 2-methylimidazole hydrochloride in 20 ml of ethanol with stirring. When the addition was complete, the resultant mixture was stirred for one hour to complete the reaction. The reaction solution was then distilled to remove the solvent, and the crystals thus deposited were triturated with 50 ml of water, filtered off, washed with water and dried to give 4.3 g (yield 90.2%) of the titled compound as colorless crystal. Melting point 205° to 207° C.

Elemental analysis: Found: C, 70.5%; H 5.0%. Calcd.: C, 70.9%; H 4.9%.

EXAMPLE 5

Production of tetra(4-fluorophenyl)boron-2-methylimidazolium complex (Compound No. 8)

The procedure of Example 4 was repeated except that ethanol was replaced by iso-propylalcohol as the reaction solvent. There was afforded 4.4 g of the titled compound as colorless crystal. M.p. 205° to 207° C.

Elemental analysis: Found: C, 70.5%; H, 5.0%. Calcd.: C, 70.9%; H, 4.9%.

EXAMPLE 6

Production of tetra(4-methylphenyl)boron-pyridinium complex (Compound No. 1)

A flask of 500 ml capacity was charged with a solution of 19.9 g (0.05 moles) of tetra(methylphenyl)boron sodium in 200 ml of tetrahydrofuran, to which was added dropwise an aqueous solution (50 ml) of 4.0 g (0.05 moles) of pyridine and equimolar proportion of aqueous hydrochloric acid in water with stirring. Subsequently, the reaction solution was treated in the same manner as in Example 2, affording 20.8 g (yield: 91.3%) of the titled compound as colorless crystal. M.p. 183° to 185° C.

Elemental analysis: Found: C, 86.8%; H, 7.4%. Calcd.: C, 87.0%; H, 7.5%.

EXAMPLE 7

Production of triphenyl-(4-vinyl)phenylboron-2-methylimidazolium complex (Compound No. 10 of Table 1)

Triphenyl-(4-vinyl)phenylboron sodium (0.05 moles) was reacted with 2-methylimidazole hydrochloride (0.05 moles) in the similar manner to that of Example 4 using acetone as the reaction solvent to give 20.0 g (yield: 93.7%) of the titled compound as colorless crystal. M.p. 234° to 236° C.

Elemental analysis: Found: C, 84.1%; H, 6.9%. Calcd.: C, 84.2%; H, 6.8%.

Other compounds of general formula (I) referred to in Table 1 were also prepared in the same manner as those given in Examples 2-7 above.

ANTIFOULING PAINT COMPOSITIONS

As explained hereinbefore, the tetraarylboron-ammonium complexes of general formula (I) according to this invention possess a markedly long-term antifouling activity with a low toxicity and are therefore useful as antifouling agent or as active ingredient of antifouling paint compositions. It is worthy of special mention that the complex compounds of this invention will bring little or no problems in toxicity and skin-irritation for human beings during the preparation and application of paint compositions containing them and in environmental pollutions. Further, the antifouling paint composition according to this invention possesses many advantageous properties such that it exhibits substantially no selective toxicity against aquatic organisms, thus high antifouling activity against substantially all those organisms and also against slimes, that the antifouling activity thereof is significantly long-lasting and that it is non-corrosive on various light alloys and thus applicable for painting ship's hull made of light alloys with safety.

The anti-fouling paint according to this invention may contain, in addition to the active ingredient compound of the formula (I), other known copper-, organotin- and/or dithiocarbamate-antifouling agents. Typical examples of those known antifouling agents include copper-antifouling agent such as cuprous oxide, copper rhodanide, copper hydroxide and metallic copper, and tin-antifouling agent such as bis-(tributyltin)oxide, tributyltin chloride, tributyltin fluoride, tributyltin acetate, tributyltin nicotinate, tributyltin versatate, bis-(tributyltin)-$\alpha,\alpha'$-dibromosuccinate, triphenyltin hydroxide, triphenyltin chloride, triphenyltin fluoride, triphenyltin acetate, triphenyltin nicotinate, triphenyltin dimethyldithiocarbamate, triphenyltin versatate, bis-(triphenyltin)-$\alpha,\alpha'$-dibromosuccinate and bis-(triphenyltin)oxide. Typical examples of dithiocarbamate anti-fouling agent include tetramethyltiuram monosulfide (hereinafter abbreviated as TS), tetramethyltiuram disulfide, zinc bis-(dimethyldithiocarbamate) (hereinafter abbreviated as 2 DMC), zinc ethylene-bis(dithiocarbamate) (hereinafter, abbreviated as 2TNEB), manganese ethylene-bis(-dithiocarbamate) and copper bis-(dimethyldithiocarbamate) (hereinafter abbreviated as TTCu).

Suitably, the active compound of the formula (I) is present in a proportion of 0.5 to 50% by weight, preferably 1 to 30% by weight of the total weight of the paint composition, in association with the resinous vehicle for paints.

The resin vehicle available in the anti-fouling paint according to this invention may be any of those vehicles as conventionally used in the usual antifouling paints. They may be, for example, vinyl chloride resin, chlorinated rubber resin, chlorinated polyethylene resin, chlorinated polypropylene resin, acrylic resin, styrenebutadiene resin, polyester resin, epoxy resin, polyamide resin, petroleum resin, oleoresin, rosin ester, rosin soap and rosin. As a vehicle having anti-fouling properties by itself, there may also be used such an acrylic copolymer resin comprising as the component unit a complex of organotin compound with a polymerizable unsaturated carboxylic acid, which is obtained by reacting the polymerizable unsaturated carboxylic acid such as (meth)acrylic acid with the organotin compound such as bis(tributyltin)oxide and triphenyltin hydroxide.

Besides, the anti-fouling paint according to this invention may contain optional proportions of plasticizer, color pigment, extender pigment, solvent and the like which are conventionally employed in the art of the antifouling paints.

The antifouling paint according to this invention may be prepared in a manner known per se in the technical field of manufacturing paints. The compounding of the various components may be carried out using known blending machines such as ball mill, pebble mill, roller mill and high-speed run mill.

The antifouling paint composition according to this invention is illustrated by the following Examples 8 to 23 in which "parts" represents "parts by weight" unless otherwise stated. Examples 24 to 28 are given for comparison purposes to show some conventional paint formulations comprising as active ingredient known antifouling compounds alone or in admixture with other compounds.

EXAMPLE 8

20 Parts of Compound No. 1 (see Table 1), 7 parts of VAGH (a vinyl chloride resin available from Union Carbide Company, U.S.A.; hereinafter abbreviated as VAGH), 6 parts of W.W. rosin, 1 part of colloidal silica, 4 parts of red iron oxide, 5 parts of titanium oxide, 20 parts of zinc white, 2 parts of dioctyl phthalate, 30 parts of xylene and 5 parts of methylisobutylketone were uniformly mixed together to prepare a desired antifouling coating formulation.

EXAMPLES 9 TO 18

The above mentioned ingredients of Example 8 were uniformly blended together in the same proportions as in Example 8 except that Compound No. 1 was replaced by Compound Nos. 2 to 11 of Table 1, respectively, whereby several antifouling paint formulations were prepared.

EXAMPLE 19

10 Parts of Compound No. 7, 20 parts of cuprous oxide, 40 parts of a TBT-acryl copolymer solution (which was obtained by dissolving a mixture of 65 parts of tributyltin methacrylate and 35 parts of methyl methacrylate in 60 parts of xylene, followed by adding thereto 0.35 parts of benzoyl peroxide and polymerization until a viscosity of 4.5 poise at 25° C. was reached; hereinafter abbreviated as TBT-acryl copolymer solution), 1 parts of colloidal silica, 5 parts of titanium oxide, 10 parts of zinc white and 14 parts of xylene were uniformly mixed together to prepare a desired antifouling paint formulation.

EXAMPLE 20

An antifouling paint formulation was prepared by repeating the procedure of Example 19 except that Compound No. 7 was replaced by Compound No. 8.

EXAMPLE 21

10 Parts of Compound No. 9, 38 parts of cuprous oxide, 6 parts of VAGH, 6 parts of W.W. rosin, 1 part of colloidal silica, 4 parts of red iron oxide, 5 parts of zinc white, 2 parts of dioctyl phthalate, 23 parts of xylene and 5 parts of methylisobutylketone were uniformly mixed together to prepare an antifouling paint formulation according to this invention.

EXAMPLE 22

10 Parts of Compound No. 10, 5 parts of triphenyltin chloride, 7 parts of VAGH, 6 parts of W.W. rosin, 1 part of colloidal silica, 4 parts of red iron oxide, 5 parts of titanium oxide, 25 parts of zinc white, 2 parts of dioctyl phthalate, 30 parts of xylene and 5 parts of methylisobutylketone were uniformly mixed together to prepare an antifouling paint formulation according to this invention.

EXAMPLE 23

5 Parts of Compound No. 11, 10 parts of cuprous oxide, 5 parts of triphenyltin chloride, 7 parts of VAGH, 6 parts of W.W. rosin, 1 part of colloidal silica, 4 parts of red iron oxide, 5 parts of titanium oxide, 20 parts of zinc white, 2 parts of dioctyl phthalate, 30 parts of xylene and 5 parts of methylisobutylketone were uniformly mixed together to prepare an antifouling paint formulation according to this invention.

EXAMPLE 24

(Comparative)

This Example is given for comparison purpose. 40 Parts of cuprous oxide, 7 parts of VAGH, 6 parts of W.W. rosin, 1 part of colloidal silica, 4 parts of red iron oxide, 5 parts of titanium oxide, 2 parts of dioctyl phthalate, 30 parts of xylene and 5 parts of methylisobutylketone were uniformly mixed together to prepare an antifouling paint composition as comparative sample.

EXAMPLE 25

(Comparative)

This Example is given for comparison purpose. 20 Parts of triphenyltin chloride, 7 parts of VAGH, 6 parts of W.W. rosin, 1 part of colloidal silica, 4 parts of red iron oxide, 5 parts of titanium oxide, 20 parts of zinc white, 2 parts of dioctyl phthalate, 30 parts of xylene and 5 parts of methylisobutylketone were uniformly mixed together to prepare a conventional antifouling paint composition.

EXAMPLE 26

(Comparative)

This Example is given for comparison purpose. 38 Parts of cuprous oxide, 10 parts of triphenyltin chloride, 6 parts of VAGH, 6 parts of W.W. rosin, 1 part of colloidal silica, 4 parts of red iron oxide, 5 parts of titanium oxide, 2 parts of dioctyl phthalate, 23 parts of xylene and 5 parts of methylisobutylketone were uniformly mixed together to prepare a conventional antifouling paint composition.

EXAMPLE 27

(Comparative)

This Example is given for comparison purpose. 20 Parts of tetraphenylboron pyridinium complex of the formula

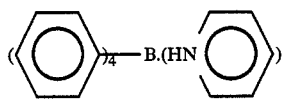

(This compound was disclosed in Japanese Patent Publication No. 1571/79), 7 parts of VAGH, 6 parts of W.W. rosin, 1 part of colloidal silica, 4 parts of red iron oxide, 5 parts of titanium oxide, 20 parts of zinc white, 2 parts of dioctyl phthalate, 30 parts of xylene and 5 parts of methylisobutylketone were uniformly mixed together to prepare an antifouling paint composition of the prior art.

EXAMPLE 28

(Comparative)

This Example is given for comparison purpose. A commercially available product of chlorinated rubber-based antifouling paint was purchased and used for the tests.

The antifouling performance of typical complex compounds of general formula (I) according to this invention as active ingredient of antifouling paint is now illustrated by a series of tests given in Example 29.

EXAMPLE 29

This Example was carried out to test the various antifouling paints for their performance of preventing the fouling aquatic organisms from attaching to and growing on aquatic structures as well as for their performance of preventing the fouling slimes from attaching to the aquatic articles.

Each of the antifouling paint formulations as prepared in Examples 8 to 23 was applied as one coat to 100×300 mm steel trial panels which had been precoated with a corrosion-resistant paint (a commercially available ship bottom paint No. 1 based on coal tar/vinyl chloride resin) so that the thickness of the dried film of the antifouling paint was from 60 to 80 microns, and the coat was dried for 24 hours. Two experiments were then carried out where the resultant coated steel panels were hanging from and secured to a test raft off Uno Harbour, Tamano City, Okayama Prefecture, Japan in such way that the panels were immersed in sea water at 0.5 meter depth below the water surface and at 1.5 meters depth below the water surface. The test panels at 1.5 meters depth were visually inspected at monthly intervals and assessed to determine the amount of the attaching and growing aquatic small animals such as barnacles and serpulae and the amount of the attaching and growing aquatic plants such as green laver and sea lettuce, in term of the rate (percent) of the fouled area covered by the fouling aquatic animals and plants. The test panels at 0.5 meter depth were used to evaluate the slime-resistant properties thereof, and they were visually inspected and assessed to determine the change in the amount of the attaching slimes, in term of the rate (percent) of the fouled area covered by the fouling slimes.

For comparison, the above procedure was repeated using the conventional anti-fouling paints (Examples 24 to 27) comprising as active ingredient the known antifouling compounds, as well as the commercially available chlorinated rubber-based antifouling paint (Example 28) comprising both of cuprous oxide and an organotin compound.

The testing period was two years from April 1981 to April 1983.

The results of assessment of the change in the amount of the attaching and growing aquatic organisms (the immersion tests at 1.5 meters depth in water) are shown in Table 2 below and the results of assessment of the change in the amount of the attaching slimes (the tests of preventing the fouling slimes from attaching to the panels at 0.5 m depth in water) are shown in Table 3.

Now, by the term "slimes" is meant the whole of the metabolic products as viscous membrane produced by various aquatic bacteria, and of bacteria cells and of Diatomaceae. Attachment of the slimes can induce the introduction of spores of the sea lettuce and green laver or of lervae of barnacles into the slime layer, thereby promoting propagation of the fouling organisms, so that the antifouling paint must be highly effective to control the fouling slimes.

TABLE 2

| | (Immersion test at 1.5 m depth in water) | | | | |
|---|---|---|---|---|---|
| | Antifouling properties assessed by rate (%) of the area covered with fouling organisms | | | | |
| | Immersion period | | | | |
| Paint under test | 6 months | 12 months | 16 months | 20 months | 24 months |
| Example 8 | 0 | 0 | 0 | 0 | 5 |
| Example 9 | 0 | 0 | 0 | 0 | 5 |
| Example 10 | 0 | 0 | 0 | 0 | 0 |
| Example 11 | 0 | 0 | 0 | 0 | 0 |
| Example 12 | 0 | 0 | 0 | 0 | 0 |
| Example 13 | 0 | 0 | 0 | 0 | 0 |
| Example 14 | 0 | 0 | 0 | 0 | 0 |
| Example 15 | 0 | 0 | 0 | 0 | 0 |
| Example 16 | 0 | 0 | 0 | 0 | 0 |
| Example 17 | 0 | 0 | 0 | 0 | 0 |

TABLE 2-continued (Immersion test at 1.5 m depth in water)
Antifouling properties assessed by rate (%)
of the area covered with fouling organisms

| Paint under test | Immersion period | | | | |
|---|---|---|---|---|---|
| | 6 months | 12 months | 16 months | 20 months | 24 months |
| Example 18 | 0 | 0 | 0 | 0 | 0 |
| Example 19 | 0 | 0 | 0 | 0 | 0 |
| Example 20 | 0 | 0 | 0 | 0 | 0 |
| Example 21 | 0 | 0 | 0 | 0 | 0 |
| Example 22 | 0 | 0 | 0 | 0 | 0 |
| Example 23 | 0 | 0 | 0 | 0 | 0 |
| Example 24 (Comparative) | 0 | 20 | 40 | 100 | 100 |
| Example 25 (Comparative) | 5 | 25 | 50 | 100 | 100 |
| Example 26 (Comparative) | 0 | 10 | 40 | 100 | 100 |
| Example 27 (Comparative) | 0 | 5 | 20 | 45 | 90 |
| Example 28 (Comparative) | 0 | 15 | 30 | 50 | 100 |

TABLE 3

Test of preventing the fouling slimes at 0.5 m depth in water
Rate (%) of area covered by the fouling
slimes at 0.5 m depth in water

| Paint | Immersion period | | | | |
|---|---|---|---|---|---|
| | 3 months | 6 months | 9 months | 12 months | 15 months |
| Example 8 | 0 | 0 | 0 | 5 | 20 |
| Example 9 | 0 | 0 | 0 | 0 | 20 |
| Example 10 | 0 | 0 | 0 | 5 | 50 |
| Example 11 | 0 | 0 | 0 | 5 | 20 |
| Example 12 | 0 | 0 | 0 | 10 | 100 |
| Example 13 | 0 | 0 | 0 | 5 | 50 |
| Example 14 | 0 | 0 | 0 | 0 | 30 |
| Example 15 | 0 | 0 | 0 | 5 | 30 |
| Example 16 | 0 | 0 | 0 | 0 | 10 |
| Example 17 | 0 | 0 | 0 | 0 | 10 |
| Example 18 | 0 | 0 | 0 | 0 | 5 |
| Example 19 | 0 | 0 | 0 | 0 | 5 |
| Example 20 | 0 | 0 | 0 | 0 | 30 |
| Example 21 | 0 | 0 | 0 | 0 | 0 |
| Example 22 | 0 | 0 | 0 | 0 | 0 |
| Example 23 | 0 | 0 | 0 | 0 | 0 |
| Example 24 (comparative) | 20 | 50 | 100 | 100 | 100 |
| Example 25 (comparative) | 0 | 20 | 100 | 100 | 100 |
| Example 26 (comparative) | 0 | 10 | 50 | 100 | 100 |
| Example 27 (comparative) | 0 | 5 | 30 | 80 | 100 |
| Example 28 (comparative) | 0 | 20 | 50 | 100 | 100 |

ANTISEPTIC, ANTIFUNGAL AGENT

The tetraarylboron-ammonium complexes of general formula (I) according to this invention, as explained hereinbefore, also exhibit high antiseptic and antifungal activities and are thus useful as antiseptic and antifungal agents for many applications.

For applications as antiseptic, antifungal agent, the tetraarylboron ammonium complex of the formula (I) according to this invention may be formulated in a conventional manner into a form of an emulsion, flowable agent (sol composition), wettable powder, liquid preparation and the like which can subsequently be employed similarly to the known antiseptic, antifungal agent without any restriction to particular mode of use thereof, in order to develop efficiently the excellent antiseptic and antifungal activities which the new compound of this invention possesses. The proportion of the tetraarylboron complex according to this invention may optionally be selected depending upon the object for which the antiseptic, antifungal agent according to this invention is to be applied and the like.

Furthermore, the antiseptic, antifungal agent according to this invention may be used in admixture with or in combination with other known commercial antiseptic or antifungal compounds or agents. Typical examples of those known antiseptic or antifungal compounds or agents by chemical name may include zinc diethylthiol carbamate, tetramethylthiuram disulfide, tetrachloroisophthalonitrile, 2-(4-thiazolyl)benzimidazole, methylbenzimidazol carbamate, parachlorophenol, 4-tetrahexylphenol, parachlorometaxylenol, bis(2-pyridylthio-1-oxide), and 4-chlorophenyl-3-iodopropargylformal, which are merely illustrative in a non-limitative manner. Moreover, the antiseptic, antifungal agent according to this invention may also be used in admixture with or in combination with an insecticidal compound to provide a formulation having the antiseptic, antifungal and insecticidal (or insect-repelling) properties.

With reference to the following Examples, this invention is further illustrated for the antiseptic, antifungal agents of non-medical utility comprising the complex compound according to this invention.

EXAMPLE 30

This Example is given for formulating a wettable powder. 20 Parts of Compound No. 1 of Table 1, 7 parts of lauryl sulfate and 73 parts of clay were uniformly mixed and ground together to give a wettable powder comprising 20% by weight of the active ingredient.

EXAMPLE 31

This Example is given for formulating a flowable agent.

20 Parts of compound No. 6, 2 parts of lauryl sulfate, 2 parts of Xanthan-gum and 1 part of hydroxypropylcellulose were uniformly mixed together to afford a flowable agent containing 20% by weight of the active ingredient.

EXAMPLE 32

This Example is given for formulating an emulsion. 1 Part of compound No. 11, 47 parts of dimethylsulfoxide, 50 parts of tetrahydrofuran and 2 parts of Sorpol 800 A (Trade name of an emulsifying agent available from Toho Chemical Industries Co., Ltd.) were uniformly mixed together to give an emulsion containing 1% by weight of the active ingredient.

The following Examples are illustrative of the actual availability of the antiseptic, antifungal agent comprising as active ingredient the tetraarylboron ammonium complex according to this invention.

EXAMPLE 33

This Example was carried out to test the antibacterial activity of the new compounds of this invention against various microorganisms. The tests were conducted according to agar dilution smear method (streak method) for estimation of the inhibitory activity against various microorganisms, including fungi and bacteria, known as the organisms of degrading industrial materials. Thus, each test microorganism was previously incubated on a slant agar medium in test tube and then admixed with sterilized water to give a spore suspension.

A loopful amount of the resultant spore suspension was inoculated by streaking to a potato extract medium (pH 5.8) containing the compound under test for the fungi, and to a bouillon-agar medium (pH 7.0) containing the compound under test for the bacteria. The culture media thus inoculated were incubated at a temperature of 28±2° C. for 96 hours and the condition of growth of each test microorganism was observed to evaluate the minimum inhibitory concentration (MIC; ppm) of the test compound which was required to inhibit completely the growth of fungi or bacteria. The results are tabulated in Table 4 below.

growth of the fungi was evaluated on the under-mentioned grading after 3 days, 7 days and 14 days of incubation and after 3 months of storage under natural conditions (at 27° C., 98% humidity) in case of the piece of wood; and after 3 days, 7 days and 14 days from the application of the paint in case of the filter paper.

The test results are tabulated in Tables 5 and 6 below, respectively.

The degree of growth of the fungi are rated in the following grades:

3: No growth of mycelia was observed on the inoculated area of the sample or testpiece.

TABLE 4

| Test microorganisms | \multicolumn{11}{c}{MIC (ppm) Compound No.} | | | | | | | | | | |
|---|---|---|---|---|---|---|---|---|---|---|---|
| | 1 | 2 | 3 | 4 | 5 | 6 | 7 | 8 | 9 | 10 | 11 |
| Aspergillus niger | 5 | 15 | 15 | 50 | 50 | 50 | 50 | 50 | 50 | 50 | 50 |
| Aspergillus terreus | 5 | 15 | 15 | 50 | 15 | 50 | 50 | 50 | 50 | 50 | 15 |
| Penicillium citrinum | 5 | 15 | 15 | 50 | 50 | 50 | 50 | 15 | 15 | 50 | 15 |
| Penicillium funiculosum | 50 | 15 | 15 | 50 | 5 | 50 | 15 | 50 | 50 | 50 | 15 |
| Rizopus stolonifer | 50 | 50 | 50 | 50 | 15 | 50 | 1.5 | 1.5 | 50 | 50 | 50 |
| Cladosporium cladosporioides | 50 | 50 | 5 | 15 | 5 | 50 | 15 | 15 | 5 | 50 | 50 |
| Aureobasidium pullulans | 5 | 15 | 5 | 1.5 | 1.5 | 5 | 5 | 1.5 | 5 | 15 | 15 |
| Gliocladium virens | 50 | 15 | 15 | 50 | 5 | 50 | 15 | 15 | 15 | 50 | 15 |
| Chaetomium globosum | 1.5 | 15 | 15 | 50 | 5 | 50 | 15 | 5 | 15 | 50 | 15 |
| Fusarium proliferantum | 5 | 15 | 5 | 50 | 1.5 | 50 | 15 | 5 | 15 | 50 | 15 |
| Myrothecium verrucuria | 5 | 5 | 1.5 | 15 | 1.5 | 5 | 5 | 1.5 | 5 | 15 | 5 |
| Bacillus subtilis ATCC 6633 | 1.5 | 15 | 15 | 5 | 0.5 | 5 | 1.5 | 5 | 1.5 | 50 | 1.5 |
| Bacillus cereus | 1.5 | 15 | 5 | 5 | 0.5 | 5 | 1.5 | 1.5 | 5 | 50 | 1.5 |
| Escherichia coli IAM 1239 | 50 | 50 | 50 | 50 | 50 | 50 | 50 | 50 | 50 | 50 | 50 |
| Enterobacter aerogenes IAM 1063 | 0.5 | 5 | 5 | 15 | 0.5 | 5 | 5 | 1.5 | 5 | 50 | 1.5 |
| Pseudomonas aeruginosa | 50 | 50 | 50 | 50 | 50 | 50 | 50 | 50 | 50 | 50 | 50 |
| Pseudomonas fluorescens | 50 | 50 | 50 | 50 | 50 | 50 | 50 | 50 | 50 | 50 | 50 |
| Staphylococcus aureus 209P | 0.5 | 5 | 0.2 | 15 | 0.5 | 5 | 1.5 | 1.5 | 5 | 50 | 1.5 |
| Candida albicans | 15 | 50 | 50 | 50 | 50 | 50 | 50 | 15 | 50 | 50 | 50 |
| Rhodotorula minuta | 5 | 50 | 15 | 50 | 5 | 50 | 50 | 15 | 15 | 50 | 15 |
| Rhodotorula mueilaginosa | 15 | 50 | 50 | 50 | 50 | 50 | 50 | 50 | 50 | 50 | 50 |
| Rhodotorula toxensis | 15 | 50 | 15 | 50 | 15 | 50 | 15 | 5 | 50 | 50 | 50 |
| Saccharomyces serevisiae IMF 4942 | 5 | 15 | 5 | 50 | 1.5 | 5 | 1.5 | 1.5 | 5 | 50 | 5 |

EXAMPLE 34

This Example was carried out to test the antifungal activity of the emulsion paint comprising the new compounds of this invention. The wettable powder as prepared in accordance with Example 30 and containing the new compound of this invention was added to a commercially available paint formulation of emulsion type for wood to the predetermined concentrations of the antifungal compound indicated in Tables 5–6, and each of the resulting emulsion paint formulations was applied to a piece of wood and to a sheet of filter paper and dried spontaneously. The test on antifungal properties was carried out according to JIS (Japanese Industrial Standards) Z 2911-7 Paint Test. The condition of 2: The growth of mycelia was observed on portions of the inoculated area of the sample or testpiece not exceeding ⅓ of the total area.

1: The growth of mycelia was observed on portions of the inoculated area of the sample or test-piece exceeding ⅓ of the total area.

The Comparative agent A tested and set out in Tables 5 and 6 was a commercially available antifungal agent comprising as active ingredients 2% of 2,4-thiazolylbenzimidazole and 4% of 1,2-benzoisothiazolin-3-one, and the comparative agent B a commercially available antifungal agent comprising as active ingredient 10% of bis(tributyltin)oxide. These comparative agents are also referred to in the following Examples.

TABLE 5

| | (Condition of growth of fungi on wood piece) | | | | |
|---|---|---|---|---|---|
| | | \multicolumn{4}{c}{Condition of growth of fungi} | | | |
| Compound No. | Concentration (%) of active ingredient compound | 3 days later | 7 days later | 14 days later | 3 months after natural storage (27° C., 98% humidity) |
| 1 | 0.1 | 3 | 3 | 3 | 3 |
| | 0.03 | 3 | 3 | 3 | 3 |
| 2 | 0.03 | 3 | 3 | 3 | 3 |
| 3 | 0.1 | 3 | 3 | 3 | 3 |
| | 0.03 | 3 | 3 | 3 | 2 |
| 4 | 0.1 | 3 | 3 | 3 | 3 |
| | 0.03 | 3 | 3 | 3 | 2 |
| 5 | 0.1 | 3 | 3 | 3 | 3 |
| | 0.03 | 3 | 3 | 2 | 3 |
| 6 | 0.1 | 3 | 3 | 3 | 3 |
| | 0.03 | 3 | 3 | 2 | 3 |

TABLE 5-continued (Condition of growth of fungi on wood piece)

| Compound No. | Concentration (%) of active ingredient compound | Condition of growth of fungi | | | |
|---|---|---|---|---|---|
| | | 3 days later | 7 days later | 14 days later | 3 months after natural storage (27° C., 98% humidity) |
| 7 | 0.03 | 3 | 3 | 3 | 3 |
| 8 | 0.1 | 3 | 3 | 3 | 3 |
| | 0.03 | 3 | 3 | 2 | 3 |
| 9 | 0.3 | 3 | 3 | 3 | 3 |
| | 0.1 | 3 | 3 | 3 | 2 |
| | 0.03 | 3 | 3 | 3 | 2 |
| 10 | 0.3 | 3 | 3 | 3 | 3 |
| | 0.1 | 3 | 3 | 3 | 3 |
| | 0.03 | 3 | 3 | 2 | 3 |
| 11 | 0.03 | 3 | 3 | 3 | 3 |
| Comparative agent A | 0.3 | 3 | 2 | 2 | 3 |
| | 0.03 | 3 | 2 | 1 | 2 |
| Comparative agent B | 0.3 | 3 | 3 | 2 | 2 |
| | 0.03 | 3 | 1 | 1 | 1 |
| Untreated | — | 1 | 1 | 1 | 1 |

TABLE 6

(Condition of growth of fungi on filter paper)

| Compound No. | Concentration (%) of a.i. | Condition of growth of fungi | | |
|---|---|---|---|---|
| | | 3 days later | 7 days later | 14 days later |
| 1 | 0.3 | 3 | 3 | 3 |
| | 0.1 | 3 | 3 | 2 |
| | 0.03 | 3 | 3 | 2 |
| 2 | 0.1 | 3 | 3 | 3 |
| | 0.03 | 3 | 3 | 2 |
| 3 | 0.3 | 3 | 3 | 3 |
| | 0.1 | 3 | 3 | 3 |
| | 0.03 | 3 | 3 | 2 |
| 4 | 0.1 | 3 | 3 | 3 |
| | 0.03 | 3 | 3 | 2 |
| 5 | 0.3 | 3 | 3 | 3 |
| | 0.1 | 3 | 3 | 3 |
| | 0.03 | 3 | 3 | 2 |
| 6 | 0.3 | 3 | 3 | 3 |
| | 0.1 | 3 | 3 | 3 |
| | 0.03 | 3 | 3 | 2 |
| 7 | 0.1 | 3 | 3 | 3 |
| | 0.03 | 3 | 3 | 3 |
| 8 | 0.3 | 3 | 3 | 3 |
| | 0.1 | 3 | 3 | 3 |
| | 0.03 | 3 | 3 | 3 |
| 9 | 0.3 | 3 | 3 | 3 |
| | 0.1 | 3 | 3 | 3 |
| | 0.03 | 3 | 3 | 2 |
| 10 | 0.3 | 3 | 3 | 3 |
| | 0.1 | 3 | 3 | 3 |
| | 0.03 | 3 | 3 | 2 |
| 11 | 0.1 | 3 | 3 | 3 |
| | 0.03 | 3 | 3 | 2 |
| Comparative agent A | 0.3 | 3 | 2 | 2 |
| | 0.03 | 3 | 2 | 2 |
| Comparative agent B | 0.3 | 3 | 2 | 1 |
| | 0.03 | 3 | 2 | 1 |
| Untreated | — | 1 | 1 | 1 |

EXAMPLE 35

This Example was carried out to test the antiseptic effect of the new compound of this invention in adhesive pastes.

The flowable agent as prepared in accordance with Example 31 and containing the compound of this invention was added to an adhesive paste comprising 9% of carboxymethylcellulose (hereinafter abbreviated as CMC) and to an adhesive paste comprising 10% of potato starch, respectively, to the predetermined concentrations of the active ingredient (a.i.) as indicated in Tables 7-8, and each of the resultant paste formulations was uniformly mixed together, then charged into a cup made of synthetic resin, which was covered with an aluminium foil and stored in an incubator (maintained at 30° C.). After 7 days and 11 days of storage, the paste under test was inoculated by streaking to a bouillon-agar medium which was then incubated (at 37° C. for 48 hours) to assess the condition of growth of the fungi on the following scales.

The test results are tabulated in Table 7 and 8.

The scale on the degree of growth of the fungi is as follows:

+: Growth of fungi was observed in the paste.
—: No growth of fungi was observed in the paste.

The Comparative agent C tested was a commercially available antifungal agent comprising as active ingredients 20% of parachlorometaxylenol and 20% of 2-bromo-2-nitropropan-1,3-diol.

TABLE 7

(Condition of growth of fungi in CMC paste)

| Compound No. | Concentration (ppm) of a.i. | Condition of growth of fungi | | |
|---|---|---|---|---|
| | | 3 days later | 7 days later | 11 days later |
| 1 | 2000 | — | — | — |
| | 600 | — | — | — |
| 2 | 600 | — | — | — |
| 3 | 600 | — | — | — |
| 4 | 2000 | — | — | — |
| | 600 | — | — | — |
| 5 | 2000 | — | — | — |
| | 600 | — | — | — |
| 6 | 2000 | — | — | — |
| | 600 | — | — | — |
| 7 | 600 | — | — | — |
| 8 | 2000 | — | — | — |
| | 600 | — | — | — |
| 9 | 600 | — | — | — |
| 10 | 2000 | — | — | — |
| | 600 | — | — | — |
| 11 | 2000 | — | — | — |
| | 600 | — | — | — |
| Comparative agent A | 2000 | — | + | + |
| | 600 | + | + | + |
| Comparative agent C | 2000 | + | + | + |
| Untreated | — | + | + | + |

TABLE 8

(Condition of growth of fungi in potato starch paste)

| Compound No. | Concentration (ppm) of a.i. | Condition of growth of fungi | | |
|---|---|---|---|---|
| | | 3 days later | 7 days later | 11 days later |
| 1 | 200 | − | − | − |
|   | 60 | − | − | − |
| 2 | 60 | − | − | − |
| 3 | 200 | − | − | − |
|   | 60 | − | − | − |
| 4 | 200 | − | − | − |
|   | 60 | − | − | − |
| 5 | 60 | − | − | − |
| 6 | 200 | − | − | − |
|   | 60 | − | − | − |
| 7 | 200 | − | − | − |
|   | 60 | − | − | − |
| 8 | 200 | − | − | − |
|   | 60 | − | − | − |
| 9 | 60 | − | − | − |
| 10 | 200 | − | − | − |
|   | 60 | − | − | − |
| 11 | 60 | − | − | − |
| Comparative agent A | 200 | − | − | + |
|  | 60 | − | + | + |
| Comparative agent C | 200 | − | + | + |
|  | 60 | − | + | + |
| Untreated | — | + | + | + |

EXAMPLE 36

This Example was carried out to test the effects of the compounds of this invention for controlling the growth of fungi in timber.

The testing procedure was in accordance with the test method of determining the effectiveness of the antifungal agent for timber, which was disclosed in the "Japan Wood Storage Association", Standards No. 2 (published in 1978). Thus, the emulsion as prepared according to Example 32 and containing the compound under test was diluted with a volume of xylene to the determined concentrations of the active ingredient (a.i.) compound as indicated in Tables 9–10. One piece of wood (2.5 cm × 2.5 cm × 0.5 cm piece of pine wood) had previously been immersed in a potato extract (containing 20% of potato starch and 2% of glucose; hereinafter abbreviated as PD medium) for 3 minutes to absorb the nutritive solution and then dried at 60° C., whereas other piece of wood (2.5 cm × 2.5 cm × 0.5 cm piece of pine wood) had not been immersed in such PD medium and so had not absorbed the nutrient. Those two pieces of wood were immersed into the xylene-diluted emulsions as prepared above, to absorb the a.i. compound. The wood pieces were then air-dried for 2 days to provide the pieces of wood as specimens.

Those specimens each were placed in a petri dish and coated by brush with 1 ml aliquots of such a spore suspension of a mixture of the spores of test microorganisms; *Aspergillus niger* ATCC 9642, *Penicillium funiculosum* ATCC 9644, *Rizopus stolonifer* IFO 6354, *Aureobasidium pullulans* IFO 6353, *Gliocladium virens* ATCC 9645, which had been prepared by mixing together four spore suspensions each containing the spores of each species of the microorganisms in the same aliquots. The inoculated specimens were incubated on a potato extract-agar medium specified in the JIS Z 2911. The petri dish containing the inoculated specimens was covered with a lid and incubated at a temperature of 26±2° C. and a humidity 70 to 80%. The condition of growth of the fungi was evaluated after 3 days, 7 days, 14 days and 21 days of incubation on the following grading.

The test results are summarized in Tables 9 and 10 below.

The grading on the degree of growth of the fungi is as follows:

3: No growth of the fungi was observed completely on the specimen.

2: The growth of the fungi was observed only on the lateral faces of the specimen.

1: The growth of the fungi was observed on an area not exceeding ⅓ of the total top surface of the specimen.

0: The growth of the fungi was observed on an area exceeding ⅓ of the total top surface of the specimen.

Comparative agent D tested was a commercially available antifungal agent comprising as active ingredients 2% of 2,4-thiazolylbenzimidazole, 4% of 1,2-benzoisothiazolin-3-one and 1% of diiodomethyl paratolylsulfone.

TABLE 9

(Condition of growth of fungi on specimen impregnated with PD medium)

| Compound No. | Concentration (ppm) of active compound | Condition of growth of fungi | | | | |
|---|---|---|---|---|---|---|
| | | 3 days later | 7 days later | 14 days later | 21 days later | 28 days later |
| 1 | 1000 | 3 | 3 | 3 | 3 | 3 |
| 2 | 1000 | 3 | 3 | 3 | 3 | 3 |
| 3 | 1000 | 3 | 3 | 3 | 3 | 3 |
| 4 | 1000 | 3 | 3 | 3 | 3 | 3 |
| 5 | 1000 | 3 | 3 | 3 | 3 | 3 |
| 6 | 1000 | 3 | 3 | 3 | 3 | 3 |
| 7 | 1000 | 3 | 3 | 3 | 3 | 3 |
| 8 | 1000 | 3 | 3 | 3 | 3 | 3 |
| 9 | 1000 | 3 | 3 | 3 | 3 | 3 |
| 10 | 1000 | 3 | 3 | 3 | 3 | 3 |
| 11 | 1000 | 3 | 3 | 3 | 3 | 3 |
| Comparative agent A | 10000 | 0 | 0 | 0 | 0 | 0 |
| Comparative agent B | 1000 | 3 | 3 | 2 | 2 | 1 |
| Comparative agent D | 10000 | 0 | 0 | 0 | 0 | 0 |
| Untreated | — | 0 | 0 | 0 | 0 | 0 |

TABLE 10

| | | (Condition of growth of fungi on specimen not impregnated with PD medium) | | | | |
|---|---|---|---|---|---|---|
| | Concentration | Condition of growth of fungi | | | | |
| Compound No. | (ppm) of active compound | 3 days later | 7 days later | 14 days later | 21 days later | 28 days later |
| 1 | 1000 | 3 | 3 | 3 | 3 | 3 |
| 2 | 1000 | 3 | 3 | 3 | 3 | 3 |
| 3 | 1000 | 3 | 3 | 3 | 3 | 3 |
| 4 | 1000 | 3 | 3 | 3 | 3 | 3 |
| 5 | 1000 | 3 | 3 | 3 | 3 | 3 |
| 6 | 1000 | 3 | 3 | 3 | 3 | 3 |
| 7 | 1000 | 3 | 3 | 3 | 3 | 3 |
| 8 | 1000 | 3 | 3 | 3 | 3 | 3 |
| 9 | 1000 | 3 | 3 | 3 | 3 | 3 |
| 10 | 1000 | 3 | 3 | 3 | 3 | 3 |
| 11 | 1000 | 3 | 3 | 3 | 3 | 3 |
| Comparative agent A | 10000 | 1 | 0 | 0 | 0 | 0 |
| Comparative agent B | 1000 | 3 | 2 | 2 | 2 | 1 |
| Comparative agent D | 1000 | 3 | 2 | 1 | 1 | 0 |
| Untreated | — | 0 | 0 | 0 | 0 | 0 |

What we claim is:

1. A tetraarylboron-ammonium complex having the formula (I):

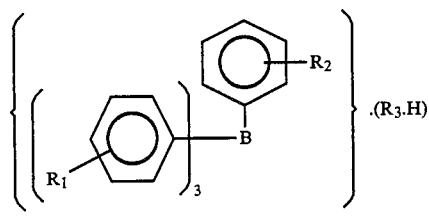

wherein $R_1$ represents a hydrogen or a halogen atom or a lower alkyl group; $R_2$ represents a halogen atom or a lower alkyl or a lower alkenyl group; and $R_3$ represents a five- or 6-membered nitrogen-containing heterocyclic ring selected from pyridine, imidazole, and methylimidazole.

2. A tetraarylboron-ammonium complex as claimed in claim 1 wherein $R_1$ is a hydrogen, chlorine or fluorine atom or methyl group; $R_2$ represents a chlorine or fluorine atom, methyl, isopropyl or vinyl group; and $R_3$ represents pyridine or 2-methylimidazole.

3. A tetraarylboron-ammonium complex selected from:
tetra(4-methylphenyl)boron-pyridinium complex;
tetra(4-methylphenyl)boron-2-methylimidazolium complex;
tetra(3-methylphenyl)boron-pyridinium complex;
tetra(3-methylphenyl)boron-2-methylimidazolium complex;
tetra(4-chlorophenyl)boron-pyridinium complex;
tetra(4-chlorophenyl)boron-2-methylimidazolium complex;
tetra(4-fluorophenyl)boron-pyridinium complex;
tetra(4-fluorophenyl)boron-2-methylimidazolium complex;
triphenyl-(4-vinyl)phenyl-boron-pyridinium complex;
triphenyl-(4-vinyl)phenyl-boron-2-methylimidazolium complex; and
triphenyl-(4-isopropyl)phenyl-boron-pyridinium complex.

4. An antifouling paint comprising as active ingredient a tetraarylboron-ammonium complex having the formula (I):

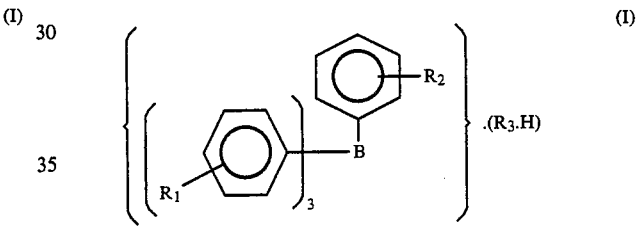

wherein $R_1$ represents a hydrogen atom, a halogen atom or a lower alkyl group; $R_2$ represents a halogen atom, a lower alkyl group or a lower alkenyl group; and $R_3$ represents a five- or 6-membered nitrogen-containing heterocyclic ring selected from pyridine, imidazole and methylimidazole in admixture with a paint base composition.

5. An antiseptic, antifungal agent comprising as active ingredient a tetraarylboron-ammonium complex having the formula (I):

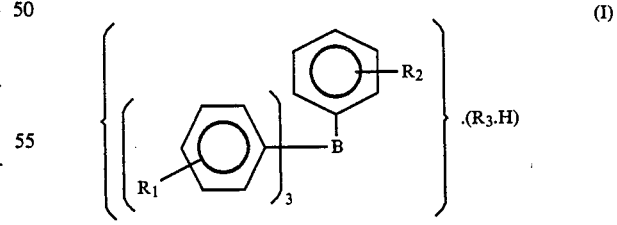

wherein $R_1$ represents a hydrogen atom, a halogen atom or a lower alkyl group; $R_2$ represents a halogen atom, a lower alkyl group or a lower alkenyl group; and $R_3$ represents a five- or 6-membered nitrogen-containing heterocyclic ring selected from pyridine, imidazole, and methylimidazole.

* * * * *